(12) United States Patent
Baba et al.

(10) Patent No.: US 9,410,795 B2
(45) Date of Patent: *Aug. 9, 2016

(54) INNER DIAMETER MEASURING DEVICE

(71) Applicant: IHI Corporation, Tokyo (JP)

(72) Inventors: Michiko Baba, Tokyo (JP); Kouzou Hasegawa, Tokyo (JP); Kiyofumi Fujimura, Tokyo (JP); Toshihiro Hayashi, Tokyo (JP); Norimasa Taga, Tokyo (JP)

(73) Assignee: IHI Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/377,238

(22) PCT Filed: Feb. 7, 2013

(86) PCT No.: PCT/JP2013/053589
§ 371 (c)(1),
(2) Date: Aug. 7, 2014

(87) PCT Pub. No.: WO2013/118911
PCT Pub. Date: Aug. 15, 2013

(65) Prior Publication Data
US 2015/0015873 A1  Jan. 15, 2015

(30) Foreign Application Priority Data

Feb. 9, 2012  (JP) .................................. 2012-026042

(51) Int. Cl.
*G01B 11/26* (2006.01)
*G01B 11/12* (2006.01)
(Continued)

(52) U.S. Cl.
CPC ................ *G01B 11/12* (2013.01); *G01B 11/24* (2013.01); *G01B 11/272* (2013.01); *G02B 23/2476* (2013.01); *G01N 2021/9544* (2013.01)

(58) Field of Classification Search
CPC ........ G01B 11/24; G01B 11/12; G01B 11/00; G01N 21/00
USPC .......................................... 356/156, 630, 626
See application file for complete search history.

(56) References Cited

U.S. PATENT DOCUMENTS

| 1,664,851 A | 4/1928 | Class |
| 1,721,524 A | 7/1929 | Moore |

(Continued)

FOREIGN PATENT DOCUMENTS

| EP | 0076144 A2 | 4/1983 |
| EP | 0973514 A1 | 6/1990 |

(Continued)

OTHER PUBLICATIONS

International Search Report and Written Opinion mailed Apr. 23, 2013 in corresponding PCT application No. PCT/JP2013/053589.

(Continued)

*Primary Examiner* — Tarifur Chowdhury
*Assistant Examiner* — Isiaka Akanbi
(74) *Attorney, Agent, or Firm* — Nields, Lemack & Frame, LLC (57) ABSTRACT

An inner diameter measuring device, comprising an image pickup unit (2) provided at a base end of a frame unit (6) and for picking up an image of a forward end side, a centering unit (4) provided at a forward end of the frame unit, a laser beam diffusing unit (5) provided on the centering unit and at a forward end side of the centering unit via a light transmitting window, a laser beam emitting unit (3) provided on a base end side of the centering unit, and a cone mirror (51) provided on the laser beam diffusing unit and having a conical reflection surface at a forward end, wherein a center line of the cone mirror coincides with an optical axis of the image pickup unit, and the centering unit is adapted to adjust a posture of the image pickup unit so that a laser beam (17) projected from the laser beam emitting unit enters a vertex of the cone mirror.

6 Claims, 7 Drawing Sheets

(51) Int. Cl.
*G01B 11/24* (2006.01)
*G02B 23/24* (2006.01)
*G01B 11/27* (2006.01)
*G01N 21/954* (2006.01)

(56) References Cited

U.S. PATENT DOCUMENTS

| | | | |
|---|---|---|---|
| 2,822,620 A | 2/1958 | Ulfeldt | |
| 3,247,732 A | 4/1966 | Barnhart | |
| 3,436,967 A | 4/1969 | Post | |
| 3,771,350 A * | 11/1973 | Romans | G01M 3/002 250/256 |
| 4,045,877 A | 9/1977 | Rutter | |
| 4,382,338 A | 5/1983 | Possati et al. | |
| 4,536,963 A | 8/1985 | Yamamoto et al. | |
| 4,631,834 A * | 12/1986 | Hayashi | G01B 5/008 33/1 M |
| 4,872,269 A * | 10/1989 | Sattmann | G01B 7/282 33/542 |
| 4,937,524 A | 6/1990 | Fasnacht et al. | |
| 4,967,092 A * | 10/1990 | Fraignier | G01B 11/303 250/559.07 |
| 5,083,384 A | 1/1992 | Possati et al. | |
| 5,095,634 A | 3/1992 | Overlach et al. | |
| 5,224,274 A | 7/1993 | Blaiklock | |
| 5,259,119 A | 11/1993 | Yoshioka et al. | |
| 5,808,250 A | 9/1998 | Torii et al. | |
| 5,933,231 A * | 8/1999 | Bieman | G01B 11/12 356/241.1 |
| 6,243,962 B1 | 6/2001 | Brock | |
| 6,249,007 B1 | 6/2001 | Gooch et al. | |
| 6,427,353 B1 | 8/2002 | Nelson et al. | |
| 6,931,149 B2 | 8/2005 | Hagene et al. | |
| 8,033,032 B2 | 10/2011 | Fujikawa et al. | |
| 8,841,603 B1 * | 9/2014 | Blanton | G01B 11/2518 250/256 |
| 8,842,297 B2 * | 9/2014 | Strksen | G01B 11/0616 250/559.22 |
| 9,145,924 B2 | 9/2015 | Baba et al. | |
| 2003/0198374 A1 | 10/2003 | Hagene et al. | |
| 2004/0114793 A1 * | 6/2004 | Bondurant | G01N 21/954 382/141 |
| 2006/0044089 A1 | 3/2006 | Kang et al. | |
| 2006/0112577 A1 | 6/2006 | Jones | |
| 2006/0283037 A1 | 12/2006 | Galle | |
| 2008/0105067 A1 * | 5/2008 | Frey | G01B 11/24 73/865.5 |
| 2009/0144999 A1 | 6/2009 | Lau | |
| 2010/0005676 A1 | 1/2010 | Fujikawa et al. | |
| 2010/0060904 A1 | 3/2010 | Keightley et al. | |
| 2010/0110448 A1 | 5/2010 | Johnson et al. | |
| 2011/0080588 A1 | 4/2011 | Segall | |
| 2015/0000465 A1 | 1/2015 | Baba et al. | |
| 2015/0002836 A1 | 1/2015 | Baba et al. | |
| 2015/0007440 A1 | 1/2015 | Baba et al. | |
| 2015/0009322 A1 | 1/2015 | Baba et al. | |
| 2015/0015695 A1 | 1/2015 | Baba et al. | |
| 2015/0020395 A1 | 1/2015 | Baba et al. | |
| 2015/0131109 A1 | 5/2015 | Baba et al. | |

FOREIGN PATENT DOCUMENTS

| | | | |
|---|---|---|---|
| EP | 1434076 | A1 | 6/2004 |
| EP | 2818825 | A1 | 8/2013 |
| FR | 2730304 | A1 | 8/1996 |
| GB | 1388475 | A | 3/1975 |
| JP | 50-159355 | A | 12/1975 |
| JP | 57-22501 | A | 2/1982 |
| JP | 58-66809 | A | 4/1983 |
| JP | 59-187155 | A | 10/1984 |
| JP | 61-144551 | A | 7/1986 |
| JP | 61-282659 | A | 12/1986 |
| JP | 63-55441 | A | 3/1988 |
| JP | 63-159708 | A | 7/1988 |
| JP | 1-195309 | A | 8/1989 |
| JP | 3-502491 | A | 6/1991 |
| JP | 5-62573 | A | 3/1993 |
| JP | 7-55426 | A | 3/1995 |
| JP | 7-29405 | U | 6/1995 |
| JP | 7-191269 | A | 7/1995 |
| JP | 8-14874 | A | 1/1996 |
| JP | 8-93876 | A | 4/1996 |
| JP | 9-311034 | A | 12/1997 |
| JP | 10-137962 | A | 5/1998 |
| JP | 10-197215 | A | 7/1998 |
| JP | 10-213404 | A | 8/1998 |
| JP | 2000-136923 | A | 5/2000 |
| JP | 2000-146564 | A | 5/2000 |
| JP | 2002-22671 | A | 1/2002 |
| JP | 2002-148036 | A | 5/2002 |
| JP | 2003-139525 | A | 5/2003 |
| JP | 2003-329606 | A | 11/2003 |
| JP | 2004-176852 | A | 6/2004 |
| JP | 3105724 | U | 11/2004 |
| JP | 2005-315814 | A | 11/2005 |
| JP | 2005-331333 | A | 12/2005 |
| JP | 2006-153546 | A | 6/2006 |
| JP | 20060156138 | A | 6/2006 |
| JP | 2006-229551 | A | 8/2006 |
| JP | 2006-234525 | A | 9/2006 |
| JP | 2007-57305 | A | 3/2007 |
| JP | 2007-71852 | A | 3/2007 |
| JP | 2007-248465 | A | 9/2007 |
| JP | 2007-292699 | A | 11/2007 |
| JP | 4230408 | B2 | 2/2009 |
| JP | 2010-164334 | A | 7/2010 |
| JP | 2011-2439 | A | 1/2011 |
| JP | 2011-13060 | A | 1/2011 |
| WO | 97/02480 | A1 | 1/1997 |
| WO | 2007051332 | A2 | 5/2007 |
| WO | 2009152851 | A1 | 12/2009 |
| WO | 2013/118918 | A1 | 8/2013 |

OTHER PUBLICATIONS

International Preliminary Report on Patentability mailed Aug. 21, 2014 in corresponding PCT application No. PCT/JP2013/053589.
International Search Report and Written Opinion mailed Apr. 2, 2013 in co-pending PCT application No. PCT/JP2013/053590.
International Preliminary Report on Patentability mailed Aug. 21, 2014 in co-pending PCT application No. PCT/JP2013/053590.
International Search Report and Written Opinion mailed Apr. 23, 2013 in co-pending PCT application No. PCT/JP2013/053591.
International Preliminary Report on Patentability mailed Aug. 21, 2014 in co-pending PCT application No. PCT/JP2013/053591.
International Search Report and Written Opinion mailed May 7, 2013 in co-pending PCT application No. PCT/JP2013/053592.
International Preliminary Report on Patentability mailed Aug. 21, 2014 in co-pending PCT application No. PCT/JP2013/053592.
International Search Report and Written Opinion mailed Mar. 12, 2013 in co-pending PCT application No. PCT/JP2013/053599.
International Preliminary Report on Patentability mailed Aug. 21, 2014 in co-pending PCT application No. PCT/JP2013/053599.
International Search Report and Written Opinion mailed May 7, 2013 in co-pending PCT application No. PCT/JP2013/053597.
International Preliminary Report on Patentability mailed Aug. 21, 2014 in co-pending PCT application No. PCT/JP2013/053597.
International Search Report and Written Opinion mailed Apr. 16, 2013 in co-pending PCT application No. PCT/JP2013/053598.
International Preliminary Report on Patentability mailed Aug. 21, 2014 in co-pending PCT application No. PCT/JP2013/053598.
International Search Report and Written Opinion mailed Apr. 2, 2013 in co-pending PCT application No. PCT/JP2013/053603.
International Preliminary Report on Patentability mailed Aug. 21, 2014 in co-pending PCT application No. PCT/JP2013/053603.
European communication dated Sep. 4, 2015 in co-pending European patent application No. 13747139.7.
European communication dated Sep. 18, 2015 in co-pending European patent application No. 13746866.6.

(56) References Cited

OTHER PUBLICATIONS

European communication dated Sep. 14, 2015 in co-pending European patent application No. 13746596.9.
European communication dated Oct. 7, 2015 in co-pending European patent application No. 13747245.2
European communication dated Sep. 9, 2015 in co-pending European patent application No. 13746053.1.
European communication dated Nov. 11, 2015 in co-pending European patent application No. 13746339.4.
European communication dated Oct. 8, 2015 in co-pending European patent application No. 13746993.8.
Office action mailed Dec. 1, 2015 in co-pending U.S. Appl. No. 14/377,227.
European communication dated Sep. 9, 2015 in corresponding European patent application No. 13746779.1.
Notice of Allowance mailed Feb. 16, 2016 in co-pending U.S. Appl. No. 14/377,237.
Notice of Allowance mailed Mar. 1, 2016 in co-pending U.S. Appl. No. 14/377,237.
Office action mailed Dec. 30, 2015 in co-pending U.S. Appl. No. 14/344,226.
Office action mailed Apr. 18, 2016 in co-pending U.S. Appl. No. 14/377,230.
Notice of Allowance mailed May 13, 2016 in co-pending U.S. Appl. No. 14/377,226.
Notice of Allowance mailed Mar. 20, 2016 in co-pending U.S. Appl. No. 14/344,227.
Office Action mailed Mar. 25, 2015 in co-pending U.S. Appl. No. 14/377,225.
Notice of Allowance mailed Jul. 13, 2015 in co-pending U.S. Appl. No. 14/377,225.

\* cited by examiner

INNER DIAMETER MEASURING DEVICE

TECHNICAL FIELD

The present invention relates to an inner diameter measuring device for measuring an inner diameter or a shape of an inner surface of a cylindrical member, particularly relates to an inner diameter measuring device for measuring a shape of an inner surface on non-contact basis.

BACKGROUND ART

As a device for measuring an inner diameter of a cylindrical member on non-contact basis, a non-contact type inner diameter measuring device is known, by which a laser beam is projected in a total circumferential direction, and an optical ring is formed on an inner surface of a cylindrical member, and an image of the optical ring is picked up, and a shape and a diameter of the optical ring are measured from the image.

Each of the Patent Document 1 and the Patent Document 2 discloses a non-contact type inner diameter measuring device, by which a laser beam is projected in a total circumferential direction, and an optical ring formed on an inner surface of a cylindrical member is picked up, and a shape and a diameter of the optical ring are measured from the image. In the inner diameter measuring device as described in each of the Patent Document 1 and the Patent Document 2, a cone mirror having a conical reflection surface is used as means for projecting a laser beam in a total circumferential direction, and the laser beam is reflected in a total circumferential direction by projecting the laser beam to a vertex of the cone mirror.

In a case where a cone mirror is used as means for projecting the laser beam in the total circumferential direction, it is necessary to make a center line of the cone mirror coincident with an optical axis of the laser beam. However, in the Patent Document 1 and the Patent Document 2, there is no special description about a method and a device to be used for making the center line of the cone mirror coincide with the optical axis of the laser beam.

To solve the problems as described above, it is an object of the present invention to provide an inner diameter measuring device, in which a laser beam is projected in a total circumferential direction by a cone mirror, and an optical ring is formed on an inner surface of a cylindrical member, and an inner diameter of the cylindrical member is measured according to the optical ring, and the inner diameter measuring device is provided with a core aligning mechanism for aligning a center line of the cone mirror with an optical axis of the laser beam.

CONVENTIONAL ART REFERENCES

Patent Document 1: JP-A-H10-197215
Patent Document 2: JP-A-2010-164334

DISCLOSURE OF THE INVENTION

The present invention relates to an inner diameter measuring device, comprising an image pickup unit provided at a base end of a frame unit and for picking up an image of a forward end side, a centering unit provided at a forward end of the frame unit, a laser beam diffusing unit provided on the centering unit and at a forward end side of the centering unit via a light transmitting window, a laser beam emitting unit provided on a base end side of the centering unit, and a cone mirror provided on the laser beam diffusing unit and having a conical reflection surface at a forward end, wherein a center line of the cone mirror coincides with an optical axis of the image pickup unit, and the centering unit is adapted to adjust a posture of the image pickup unit so that a laser beam projected from the laser beam emitting unit enters a vertex of the cone mirror.

Further, the present invention relates to an inner diameter measuring device, wherein the centering unit has an X-axis slider slidable in a direction perpendicularly crossing the optical axis of the image pickup unit, a Y-axis slider disposed on the X-axis slider perpendicularly crossing the optical axis, and being slidable in a direction perpendicularly crossing a sliding direction of the X-axis slider, and has a mounting surface of a light emitting unit formed on the Y-axis slider, and the laser beam emitting unit is mounted on the mounting surface of the light emitting unit.

Further, the present invention relates to an inner diameter measuring device, wherein the laser beam emitting unit is mounted on the mounting surface of the light emitting unit by three sets of pulling bolts and pushing bolts each disposed at three points and can adjust tilting of an optical axis of the laser beam emitting unit with respect to the center line of the cone mirror by adjusting the pulling bolts and the pushing bolts.

Further, the present invention relates to an inner diameter measuring device, wherein the centering unit is removably attached to the frame unit, the centering unit and the frame unit are mounted by engaging style, and by mounting on the frame unit, a center line of the centering unit is adapted to coincide with the optical axis of the image pickup unit.

Further, the present invention relates to an inner diameter measuring device, wherein the laser beam diffusing unit is mounted by engaging style on the centering unit, and by mounting the laser beam diffusing unit on the centering unit, the center line of the cone mirror is adapted to coincide with the center line of the centering unit.

Further, the present invention relates to an inner diameter measuring device, wherein the centering unit, the laser beam diffusing unit, and the laser beam emitting unit are integrated with each other, and under the condition that the optical axis of the laser beam emitting unit coincides with the center line of the cone mirror by the centering unit, the centering unit is mounted on the frame unit.

BEST MODE FOR CARRYING OUT THE INVENTION

Description will be given below on an embodiment of the present invention by referring to the attached drawings.

Figure 1:
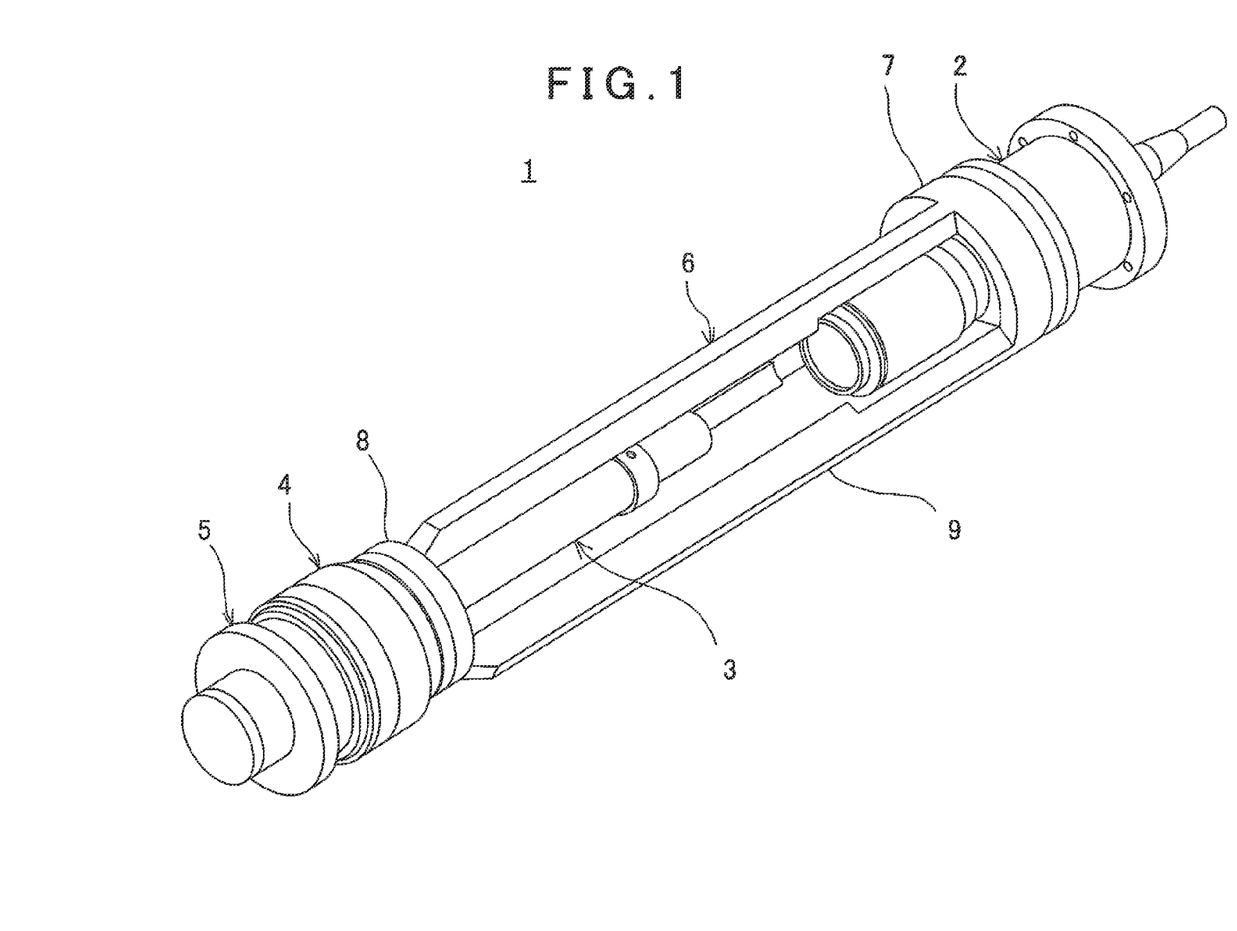
FIG. 1 is a perspective view of an embodiment of the present invention.

FIG. 1 shows an inner diameter measuring device 1 according to the embodiment of the present invention. The inner diameter measuring device 1 primarily comprises an image pickup unit 2, a laser beam emitting unit 3, a centering unit 4, a laser beam diffusing unit 5, and a frame unit 6, etc.

The frame unit 6 is so arranged that a base end ring 7 and a forward end ring 8 are connected by three support pillars 9. The support pillars 9 are disposed at a predetermined distance, e.g. at three equally divided positions on a same circumference of a circle. At a central part of the frame unit 6, a space is formed, and the image pickup unit 2 and the laser beam emitting unit 3 are arranged to be accommodated in the space. It is to be noted that there may be two or four support pillars 9 as long as the support pillars 9 can support the image pickup unit 2 and the laser beam diffusing unit 5 and no trouble occurs in an image pickup of the image pickup unit 2.

The base end ring 7 and the forward end ring 8 are concentric to each other, i.e. the base end ring 7 and the forward end ring 8 are disposed on a center line of the frame unit 6. The image pickup unit 2 is mounted on the base end ring 7 so as to penetrate the base end ring 7, and an optical axis of the image pickup unit 2 coincides with the center line of the frame unit 6.

The centering unit 4 is mounted on the forward end ring 8, and the laser beam emitting unit 3 is supported by the centering unit 4. An optical axis of the laser beam emitting unit 3 is arranged so that the optical axis coincides with the center line of the frame unit 6, i.e. the optical axis of the image pickup unit 2 under the adjusted condition.

The centering unit 4 has an adjusting mechanism unit 21 as to be described later. The laser beam emitting unit 3 is supported on the adjusting mechanism unit 21. The adjusting mechanism unit 21 is so as to enable the laser beam emitting unit 3 to displace in two directions perpendicularly crossing the optical axis of the laser beam emitting unit 3 and also has a function to adjust tilting of the optical axis of the laser beam emitting unit 3.

The laser beam diffusing unit 5 is mounted on a forward end side of the centering unit 4, and is disposed concentrically to the frame unit 6. That is, the laser beam diffusing unit 5 is arranged so as to be mounted concentrically to the image pickup unit 2 and the laser beam emitting unit 3. Further, the laser beam diffusing unit 5 is so arranged that the laser beam diffusing unit 5 is in a fixed relation with respect to the image pickup unit 2 and the frame unit 6.

Figure 2:
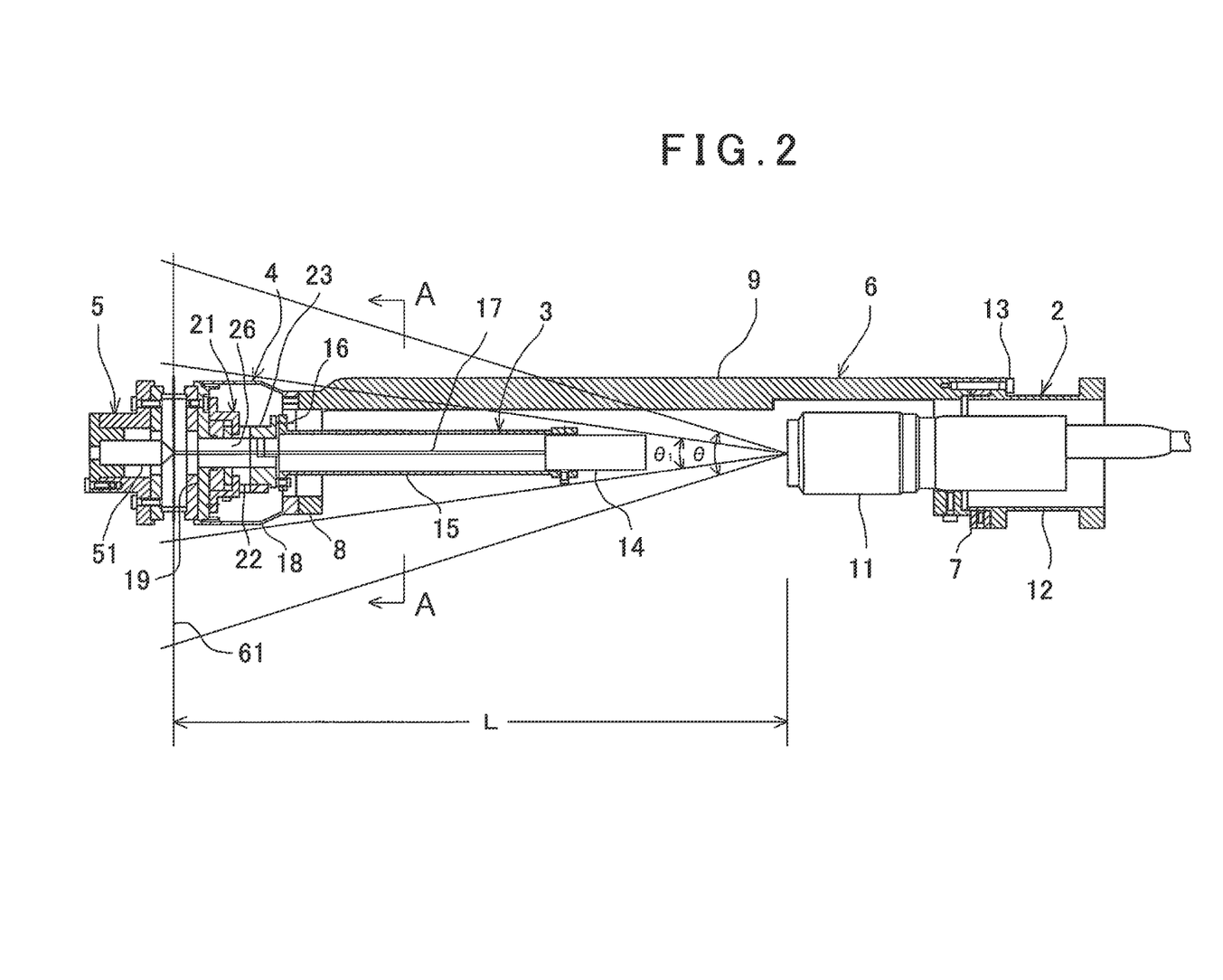
FIG. 2 is a cross-sectional view to show the embodiment.
Figure 3:
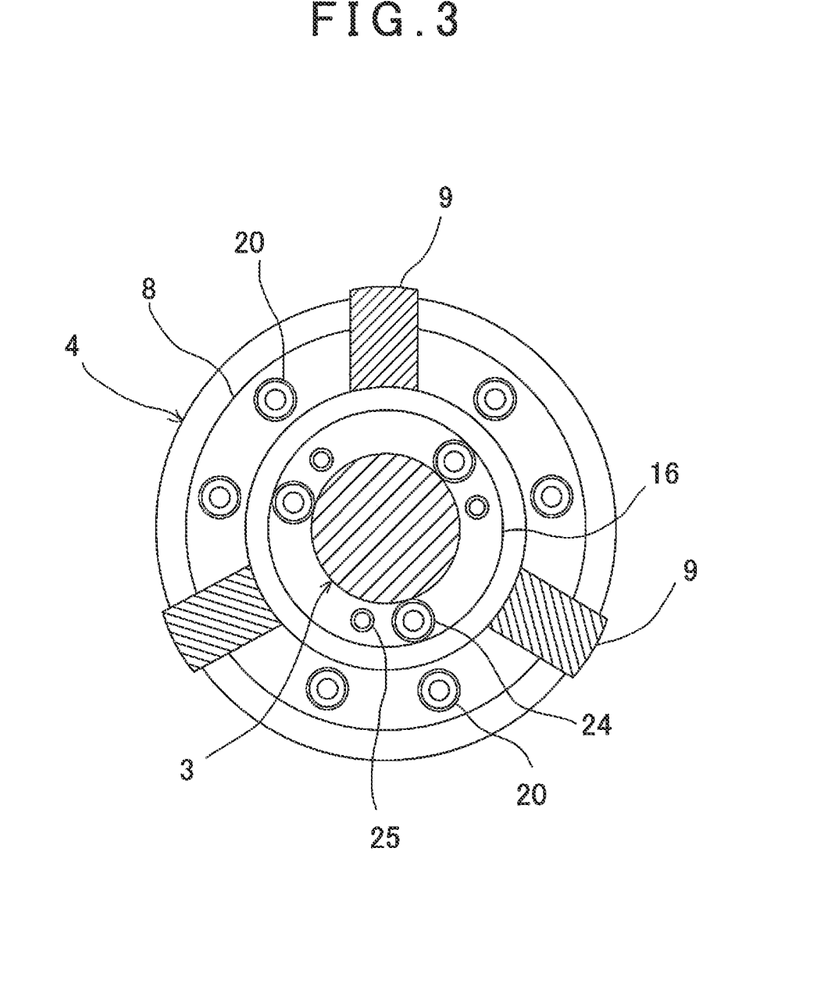
FIG. 3 is an arrow diagram along the line A-A in FIG. 2.
Figure 4:
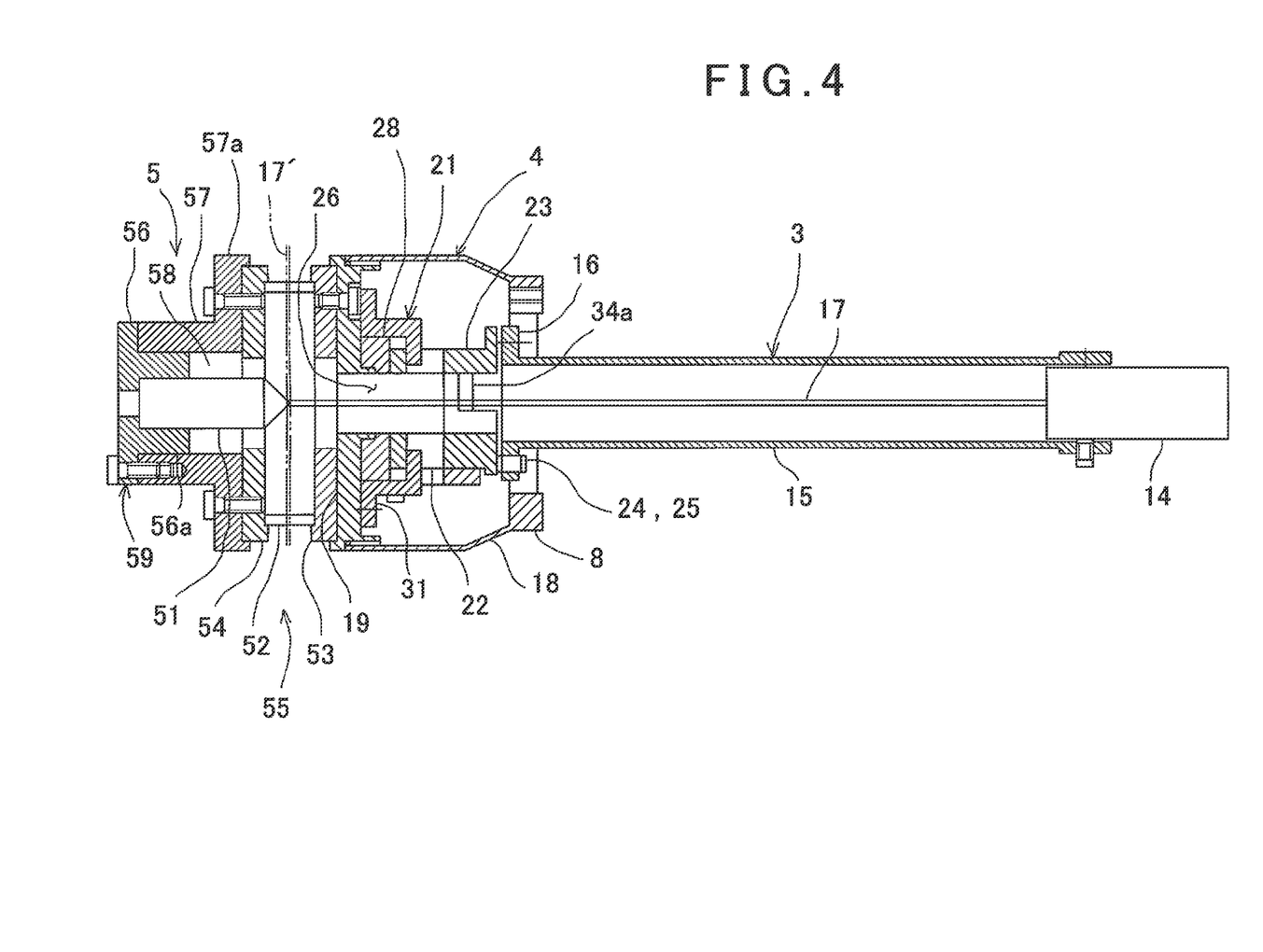
FIG. 4 is a cross-sectional view of a centering unit and a laser beam diffusing unit of the embodiment.

More concrete description will be given by referring to FIG. 2 to FIG. 4.

The image pickup unit 2 has a camera 11 and a camera accommodating member 12 for accommodating the camera 11, and the camera accommodating member 12 is fixed on the base end ring 7 by a bolt 13.

The camera 11 has a maximum field angle θ. The camera 11 has a CCD or a CMOS sensor, etc., which is an aggregate of pixels, as an image pickup element, and it is so arranged that the image pickup element outputs digital image signals, which constitute congregation of signals from each pixel, and that, signals from each pixel also can specify positions in the image pickup element respectively.

The laser beam emitting unit 3 has a laser emitter 14 for projecting a laser beam 17 as a visible light and has a laser emitter holder 15 in a shape of a hollow tube. The laser emitter 14 is engaged with and fixed on a base end portion of the laser emitter holder 15. On a forward end of the laser emitter holder 15, a fixing flange 16 is formed, and the fixing flange 16 is fixed on the adjusting mechanism unit 21 of the centering unit 4.

The centering unit 4 has a housing 18, which is a hollow cylindrical member concentric to the forward end ring 8. On a forward end side of the housing 18, a circular base member 19 is fixed, and the adjusting mechanism unit 21 is provided on the base member 19. A base end of the housing 18 is fixed on the forward end ring 8, and a bolt 20 to fix the housing 18 and the forward end ring 8 is inserted and screwed into from a base end side (on a side of the camera 11) (see FIG. 3).

Further description will be given later on the adjusting mechanism unit 21. The adjusting mechanism unit 21 has an X-axis slider 22, which can be displaced in a direction parallel to a paper surface of FIG. 2 and in a direction perpendicularly crossing the optical axis of the laser beam emitting unit 3 (in X-axis direction). The adjusting mechanism unit 21 also has a Y-axis slider 23, which is provided on the X-axis slider 22 and can be displaced in a direction perpendicular to a paper surface and also in a direction perpendicularly crossing the optical axis of the laser beam emitting unit 3 (in Y-axis direction). Therefore, the Y-axis slider 23 can be displaced in two directions perpendicularly crossing the optical axis of the laser beam emitting unit 3. An end surface of base side of the Y-axis slider 23 is served as a mounting surface of a laser beam emitting unit and the fixing flange 16 is fixed on the mounting surface of the laser beam emitting unit.

The fixing flange 16 is mounted on the Y-axis slider 23 at three points by pulling bolts 24 and pushing bolts 25. By adjusting the pulling bolts 24 and the pushing bolts 25, a tilting of the optical axis of the laser beam emitting unit 3 can be adjusted (see FIG. 3).

A cylindrical space penetrating through the central portion is formed on the adjusting mechanism unit 21. The space is continuous to a hollow portion of the laser emitter holder 15, and an optical path hole 26 for a laser beam 17 is formed by the hollow portion and the space.

Description will be given on the adjusting mechanism unit 21 by referring to FIG. 5.

On a surface of a base end side of the base member 19 (on an upper surface in FIG. 5), a center hole 26a is formed, which constitutes a part of the optical path hole 26, and an engaging ring 27, which is a protruded ridge in form of a circular ring, is formed around the center hole 26a, and a slider base 28 is fixed on the base member 19 so as to be engaged with and positioned by the engaging ring 27. On the slider base 28, a center hole 26b is formed which constitutes a part of the optical path hole 26.

On an upper surface of the slider base 28, the X-axis slider 22 is slidably disposed. On the X-axis slider 22, a center hole 26c, which is concentric to the center hole 26b and constitutes a part of the optical path hole 26, is formed, and also an X-axis guide groove 29 extending in X-axis direction is formed to penetrate the X-axis slider 22.

A pair of X-axis guides 31 and 31 are positioned on both sides of the slider base 28 and opposite to each other, and the X-axis guides 31 and 31 are fixed on the base member 19. The X-axis guide 31 is running in parallel to an upper surface of the base member 19 and has a guide portion 31a extending in X-axis direction, and the guide portion 31a is slidably engaged with the X-axis guide groove 29. A predetermined gap is formed between the X-axis guide 31 and the X-axis slider 22.

Therefore, the X-axis slider 22 is guided by the guide portion 31a and can be displaced in X-axis direction by a predetermined gap.

On an upper surface of the X-axis slider 22, the Y-axis slider 23 is slidably disposed. On the Y-axis slider 23, a center hole 26d, which is concentric to the center hole 26b and the center hole 26c and constitutes a part of the optical path hole 26, is formed, and also a Y-axis guide groove 32 extending in Y-axis direction is formed to penetrate the Y-axis slider 23. A dimension in Y-axis direction of a lower surface of the Y-axis slider 23 is set to be smaller than a dimension of the upper surface of the X-axis slider 22.

On one side surface in parallel to X-axis of the X-axis slider 22, a Y-axis guide 33 is fixed, and a Y-axis guide 34 is fixed on the other side surface in parallel to X-axis of the X-axis slider 22, and the Y-axis guide 33 and the Y-axis guide 34 are arranged at positions opposite to each other.

The Y-axis guide 33 has a guide portion 33a extending in Y-axis direction. The Y-axis guide 34 has a guide portion 34a extending in Y-axis direction, and the guide portions 33a and 34a are slidably engaged in the Y-axis guide groove 32 respectively. Between the Y-axis slider 23, the Y-axis guide 33 and the Y-axis guide 34, a gap equal to dimensional difference of the Y-axis slider 23 and the X-axis slider 22 is formed.

Therefore, the Y-axis slider 23 is guided by the guide portions 33a and 34a and can be displaced in Y-axis direction by an extent as much as the gap.

On one side surface in parallel to X-axis of the X-axis slider 22, an X-axis adjusting screw holder 35 is mounted, and an X-axis adjusting screw 36 extending in X-axis direction is mounted on the X-axis adjusting screw holder 35.

On the base member 19, an X-axis stopper holder 37 is fixed so as to face the X-axis adjusting screw holder 35, and a stopper screw 38 is mounted on the X-axis stopper holder 37. The stopper screw 38 and the X-axis adjusting screw 36 are arranged along the same center line, and a forward end of the X-axis adjusting screw 36 comes in contact with an end surface of the stopper screw 38.

On an upper surface of the slider base 28, an X-axis lock piece 39 is protruded, and the X-axis lock piece 39 is in parallel to X-axis. A long hole 41, which is long in X-axis direction, is formed on the X-axis lock piece 39.

An X-axis lock screw 42 is screwed in the X-axis slider 22 through the long hole 41. The X-axis lock screw 42 can be relatively displaced in X-axis direction by an allowance of the long hole 41 with respect to the X-axis slider 22, and this relative displacement amount is equivalent to a displacement amount of the X-axis slider 22.

Therefore, under the condition that the X-axis lock screw 42 is loosened, the X-axis slider 22 can be displaced in X-axis direction. By turning the X-axis adjusting screw 36, a protruding amount of the X-axis adjusting screw 36 is changed. Corresponding to an amount of change of the protruding amount, the X-axis slider 22 is displaced in X-axis direction, and a position of the X-axis slider 22 in X-axis direction is adjusted.

By fastening the X-axis lock screw 42, the X-axis slider 22 can be fixed on the slider base 28. After adjusting the position of the X-axis slider 22, by fastening the X-axis lock screw 42, the position of the X-axis slider 22 after adjustment is held.

On one side surface in parallel to Y-axis of the Y-axis slider 23, a Y-axis adjusting screw holder 43 is provided, and a Y-axis adjusting screw 44 extending in Y-axis direction is mounted on the Y-axis adjusting screw holder 43.

A stopper screw 45 is mounted on the Y-axis guide 34. The stopper screw 45 and the Y-axis adjusting screw 44 are arranged on the same center line, and a forward end of the Y-axis adjusting screw 44 comes in contact with an end surface of the stopper screw 45.

On one side surface of the X-axis slider 22 perpendicularly crossing X-axis, a Y-axis lock plate 46 is fixed. The Y-axis lock plate 46 is in a shape not to interfere with the guide portion 31a, and also a long hole 47, which is long in Y-axis direction, is formed.

Through the long hole 47, a Y-axis lock screw 48 is screwed into the Y-axis slider 23. The Y-axis lock screw 48 can be relatively displaced in Y-axis direction with respect to the Y-axis slider 23 by an allowance of the long hole 47, and this relative displacement amount is equivalent to a displacement amount of the Y-axis slider 23.

Therefore, under the condition that the Y-axis lock screw 48 is loosened, the Y-axis slider 23 can be displaced in Y-axis direction. By turning the Y-axis adjusting screw 44, a protruding amount of the Y-axis adjusting screw 44 is changed. Corresponding to an amount of change of the protruding amount, the Y-axis slider 23 is displaced in Y-axis direction, and a position of the Y-axis slider 23 in Y-axis direction is adjusted.

The position of the X-axis slider 22 can be adjusted in X-axis direction, and the position of the Y-axis slider 23 disposed on the X-axis slider 22 can be adjusted in Y-axis direction. Accordingly, by position adjustment through cooperative operation of the X-axis slider 22 and the Y-axis slider 23, positions of the Y-axis slider 23 in two directions of X-axis and Y-axis can be adjusted.

The laser emitter holder 15 is arranged to be mounted on an upper surface of the Y-axis slider 23, and the laser beam emitting unit 3 can be adjusted in two directions (X-axis and Y-axis directions) perpendicularly crossing the optical axis by the adjusting mechanism unit 21.

Next, the laser emitter holder 15 is fixed on the Y-axis slider 23 via the fixing flange 16. As a fixing means, the pulling bolts 24 and the pushing bolts 25 (see FIG. 3) as provided at three points are used. Therefore, by fastening the pulling bolts 24 while adjusting a protruding amount of the pushing bolts 25, tilting of the optical axis of the laser beam emitting unit 3 can be adjusted.

Figure 6:
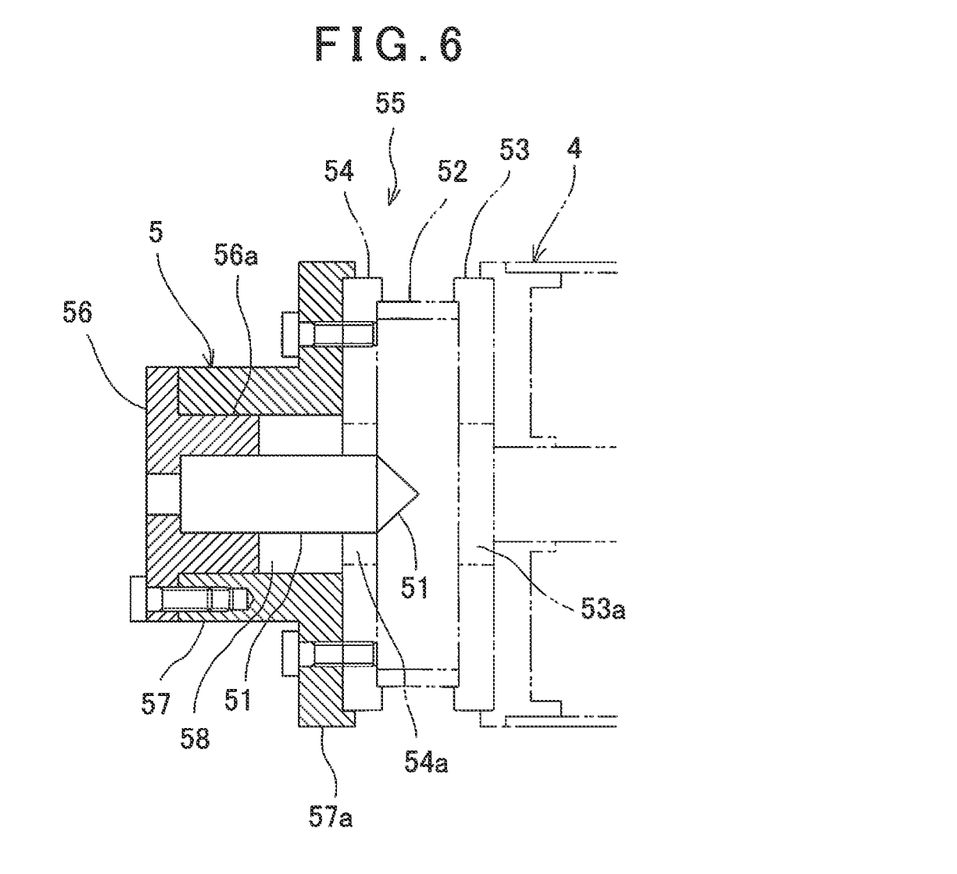
FIG. 6 is a cross-sectional view of a laser beam diffusing unit of the embodiment.

Next, description will be given on the laser beam diffusing unit 5 by referring to FIG. 4 and FIG. 6.

As to be described later, the laser beam diffusing unit 5 comprises a light transmitting window 55 and a cone mirror unit 59. The cone mirror unit 59 has a cone mirror 51, which reflects the laser beam 17 emitted from the laser emitter 14 in a total circumferential direction. The light transmitting window 55 has a total circumferential light transmitting window 52 to pass a laser beam 17' as reflected by the cone mirror 51 in a total circumferential direction.

A forward end of the cone mirror 51 at a side facing the laser emitter 14 is designed in a conical shape, and a vertical angle of the cone is set to 90°. Also, a conical surface of the forward end portion is designed as a reflection surface.

The total circumferential light transmitting window 52 is in a cylindrical shape and made of a light transmitting material such as a glass or a transparent synthetic resin. The total circumferential light transmitting window 52 is sandwiched by a first flange 53 and a second flange 54, and also, the total circumferential light transmitting window 52 is designed to be concentric to the centering unit 4. At central portions of the first flange 53 and the second flange 54, opening portions 53a and 54a concentric to the optical path hole 26, are formed, and the opening portions 53a and 54a are larger than the optical path hole 26. The total circumferential light transmitting window 52, the first flange 53 and the second flange 54 make up together a light transmitting window 55.

The cone mirror 51 is held by a cone mirror holder 56 so that a center line of the cone mirror 51 coincides with an optical axis of the laser beam 17, and the cone mirror holder 56 is arranged to be fixed on the second flange 54 via a fixing flange 57.

The cone mirror holder 56 has an engaging unit 56a. The fixing flange 57 has a flange portion 57a, and the flange portion 57a is fixed on the second flange 54 by faucet joint method. An engaging hole 58 is formed penetrating in a direction of a center line on the fixing flange 57 and the engaging unit 56*a* is arranged to be engaged in the engaging hole 58.

As described above, since the flange portion 57*a* and the second flange 54 are fixed by a faucet joint method, an accuracy of combination of the fixing flange 57 and the second flange 54 is determined by machining accuracy of the second flange 54 and the fixing flange 57. Also, since the fixing flange 57 and the cone mirror holder 56 are assembled by engaging, an assembling accuracy depends on machining accuracy of the fixing flange 57 and the cone mirror holder 56. Therefore, if under the condition that the cone mirror 51 is assembled by the cone mirror holder 56, a center line of the cone mirror holder 56 is made coincident with a center line of the cone mirror 51 with high accuracy, the center line and a vertex of the cone mirror 51 can be made coincident with the optical axis of the laser beam 17 by simply assembling the cone mirror holder 56 on the fixing flange 57 and without adjustment.

Also, if a cone mirror holder 56 holding the cone mirror 51 is assembled in advance on the fixing flange 57 and is unitized, it is guaranteed that the center line of the cone mirror 51 coincides with the optical axis of the laser beam 17 by simply assembling the fixing flange 57 on the second flange 54. The cone mirror 51, the cone mirror holder 56 and the fixing flange 57 make up together a cone mirror unit 59. It may also be so arranged that two or more cone mirror units 59 with different vertical angles of the cone mirror 51 are prepared and these cone mirror units 59 may be adequately replaced depending on the measurement conditions.

Also, the centering unit 4 can be assembled on the forward end ring 8 under the condition that the laser beam diffusing unit 5 is mounted on the centering unit 4 and the laser beam emitting unit 3 is assembled on the centering unit 4, i.e. under the condition that the centering unit 4, the laser beam diffusing unit 5 and the laser beam emitting unit 3 are unitized.

Therefore, positioning of the cone mirror 51 with respect to the laser beam 17 can be carried out under the condition of separating from the image pickup unit 2 and the frame unit 6.

Description will be given below on an operation of the inner diameter measuring device 1.

First, description will be given on an assembling of the inner diameter measuring device 1.

As described above, under the condition that the cone mirror 51 is mounted on the cone mirror holder 56 and further, that the cone mirror holder 56 is assembled on the fixing flange 57, the center line of the cone mirror 51 coincides with the center line of the fixing flange 57, i.e. the center line of the laser beam diffusing unit 5.

By mounting the cone mirror unit 59 on the light transmitting window 55, and further, by mounting the base member 19 on the first flange 53, the adjusting mechanism unit 21 can be mounted on the light transmitting window 55.

It is to be noted that because the flange portion 57*a* and the second flange 54, and also, the base member 19 and the first flange 53 are designed by the faucet joint method respectively, by mounting the cone mirror unit 59 on the light transmitting window 55, a center line of the cone mirror unit 59 is made coincident with a center line of the light transmitting window 55, and the center line of the light transmitting window 55 is arranged to be made coincident with a center line of the adjusting mechanism unit 21. It is to be noted that on the adjusting mechanism unit 21, the housing 18 is in a removed state.

Also, by fixing the laser emitter holder 15 on the Y-axis slider 23, the laser beam emitting unit 3 is mounted on the adjusting mechanism unit 21.

Under the condition that the laser beam emitting unit 3 is assembled, the center line of the cone mirror 51 is coincident with the center line of the adjusting mechanism unit 21, and the center line of the cone mirror 51 and the optical axis of the laser beam emitting unit 3 are left in a non-adjusted state.

Aligning adjustment of the center line of the cone mirror 51 and the optical axis of the laser beam emitting unit 3 is carried out by the adjusting mechanism unit 21.

Figure 5:
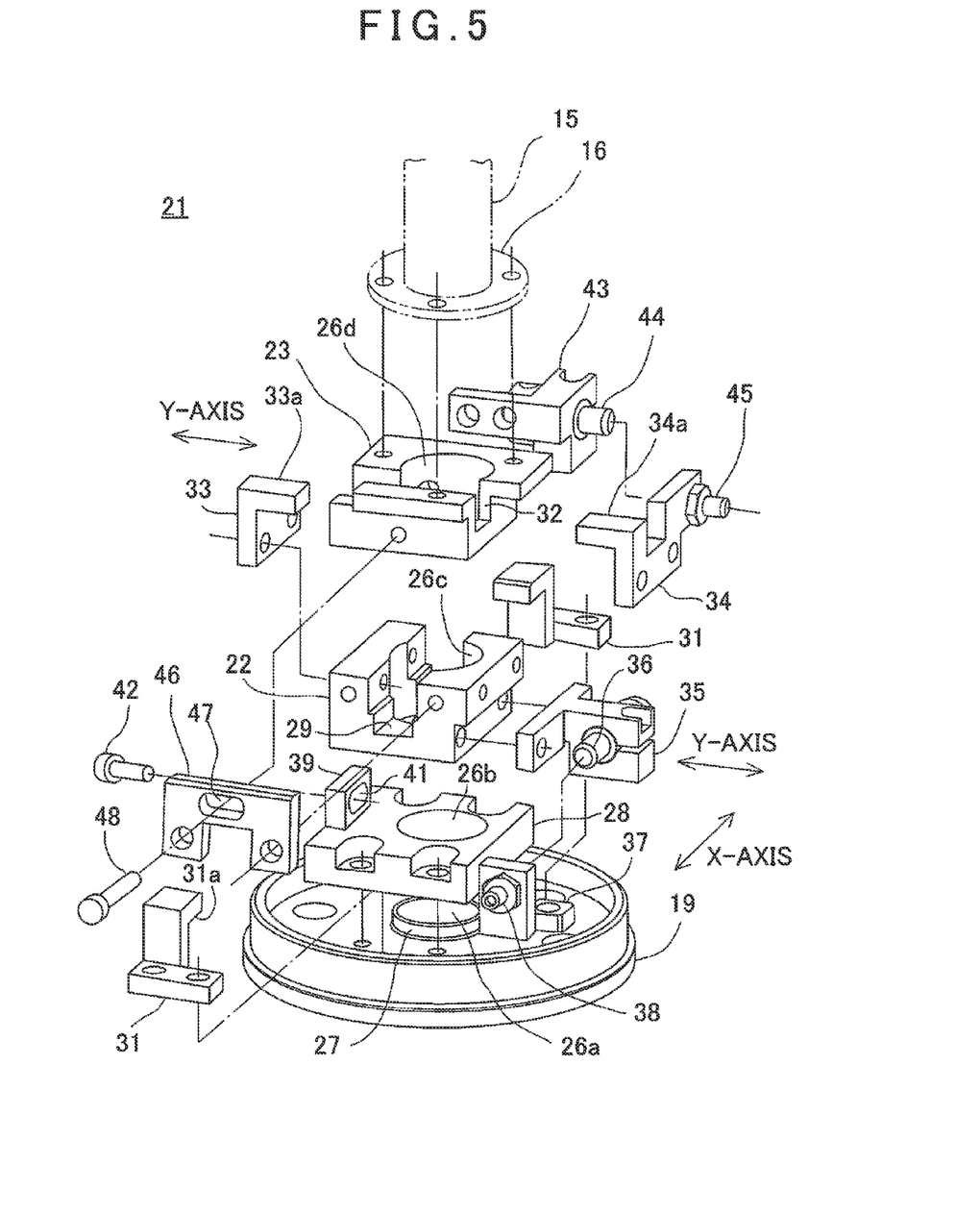
FIG. 5 is an exploded perspective view of an adjusting mechanism unit used in the embodiment.

Referring to FIG. 5, for the adjustment in X-axis direction by turning the X-axis adjusting screw 36, the protruding amount of the X-axis adjusting screw 36 is changed. Because the X-axis adjusting screw 36 comes in contact with the stopper screw 38, the X-axis slider 22 is displaced in X-axis direction, and the position is adjusted.

Also, by turning the Y-axis adjusting screw 4, the protruding amount of the Y-axis adjusting screw 44 is changed. Because the Y-axis adjusting screw 44 comes in contact with the stopper screw 45, corresponding to the protruding amount of the Y-axis adjusting screw 44, the Y-axis slider 23 is displaced in Y-axis direction, and the position is adjusted. Accordingly, by adjusting the X-axis adjusting screw 36 and the Y-axis adjusting screw 44, the position of the Y-axis slider 23 can be adjusted in two directions perpendicularly crossing the optical axis. Therefore, the position of the laser beam emitting unit 3 fixed on the Y-axis slider 23 can be adjusted in two directions perpendicularly crossing the optical axis.

By adjusting the pulling bolts 24 and the pushing bolts 25 positioned at three points, tilting of the optical axis of the laser beam emitting unit 3 with respect to the center line of the centering unit 4 can be adjusted. The pulling bolts 24 and the pushing bolts 25 fulfill the functions as optical axis adjusting unit.

By the adjustment of tilting of the optical axis of the laser beam emitting unit 3 and by the adjustment of the positions in two directions perpendicularly crossing the optical axis, the optical axis of the laser beam emitting unit 3 is made coincident with the center line of the centering unit 4.

When the optical axis of the laser beam emitting unit 3 coincides with the center line of the centering unit 4, the X-axis lock screw 42 is fastened, and the X-axis slider 22 is fixed on the slider base 28. Then, the Y-axis lock screw 48 is fastened, and the Y-axis slider 23 is fixed on the X-axis slider 22.

Then, the posture is fixed under the condition where the laser beam emitting unit 3 is aligned.

As one method to confirm whether the laser beam emitting unit 3 and the cone mirror 51 have been aligned or not and to confirm condition of adjustment in the aligning operation, an adjustment is performed under the condition where the laser beam 17 is projected from the laser beam emitting unit 3, and a laser beam 17' reflected by the cone mirror 51 is projected to a wall surface or the like, a uniformity of a ring thus formed is observed, and conditions of the aligning may be confirmed.

The housing 18 is mounted on the base member 19. Various types of methods to mount the housing 18 are thinkable. As one example, the base member 19 is screwed with the housing 18, and further, finally is engaged by the faucet joint method. Thus, fixing and aligning can be carried out. Also, under the condition where the housing 18 is fixed on the base member 19, a center line of the housing 18 coincides with the center line of the cone mirror 51.

The housing 18 is fixed on the forward end ring 8, and the image pickup unit 2 is mounted on the laser beam emitting unit 3. The image pickup unit 2 is integrated with the centering unit 4 via the frame unit 6, and the optical axis of the image pickup unit 2 coincides with the optical axis of the laser beam emitting unit 3. A faucet joint is formed on coupling portions of the housing 18 and the forward end ring 8. By simply fixing the housing 18 on the forward end ring 8, the optical axis of the image pickup unit 2 is configured to coincide with the optical axis of the laser beam emitting unit 3.

Next, description will be given on a case where an inner diameter and a shape of an inner diameter are measured by using the inner diameter measuring device 1.

Although not specifically shown in the figure, the inner diameter measuring device 1 is inserted into a hollow member such as a pipe or a hollow shaft, and further, the inner diameter measuring device 1 is supported at a center of the hollow member by a supporting device not shown in the figure.

When a laser beam 17 is projected from the laser emitter 14, the laser beam 17 enters the vertex of the cone mirror 51, and is reflected in a total circumferential direction by the cone mirror 51. The laser beam 17' thus reflected passes through the total circumferential light transmitting window 52 and is projected over total circumference.

The laser beam 17' is projected to an inner wall of the hollow member, and an optical ring 61 is formed. The optical ring 61 reflects a shape of the inner wall and by measuring a shape of the optical ring 61, a diameter and a shape (e.g. an ellipse) of the inner wall can be measured.

The camera 11 picks up an image of the optical ring 61 formed on the inner wall, and the image is outputted as an electronic image data.

The maximum field angle of the camera 11 is θmax. A central portion of an image pickup area of the camera 11 is occupied by structures such as the laser beam emitting unit 3 and the centering unit 4, etc., and images cannot be picked up about the central portion. Thus, an image pickup area F of the camera 11 has a field angle of $\theta_1 \leq F \leq \theta_{max}$, which does not interfere with the structures.

If it is supposed that a distance from a center of the field angle of the camera 11 to the vertex of the cone mirror 51 is L, a radius R of the hollow member, which can be photographed, is given as $L \tan \theta_1 \leq R \leq L \tan \theta_{max}$. Therefore, a diameter D of the hollow member, which can be measured is given as $2L \tan \theta_1 \leq D \leq 2L \tan \theta_{max}$.

An image data is inputted to an arithmetic processing device such as a PC, and the diameter and the shape of the optical ring 61 are measured based on the image data.

Figure 7:
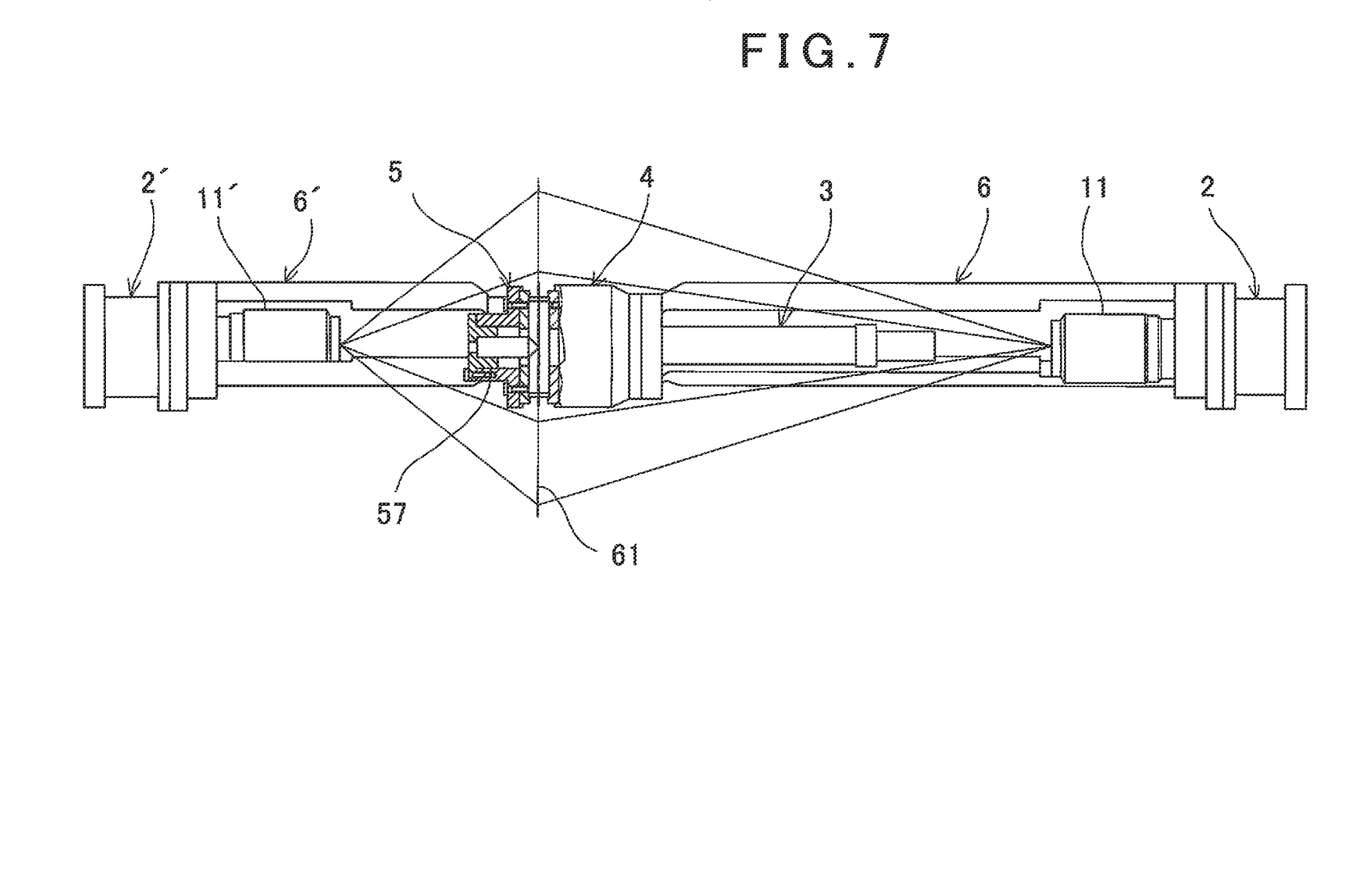
FIG. 7 is a side view of another embodiment of the present invention.

FIG. 7 shows another embodiment. In this another embodiment, one more image pickup unit 2' is mounted on the laser beam diffusing unit 5, and an optical ring 61 formed on an inner wall is arranged to be picked up from an opposite side of the image pickup unit 2. The image pickup unit 2' has a camera 11' and a frame unit 6', and a forward end of the frame unit 6' is mounted on a fixing flange 57.

By picking up an image of the optical ring 61 from the opposite side, measurement can be performed even when the inner wall has irregular surfaces and an optical ring 61 thus formed is within dead angle of the camera 11, or another case.

INDUSTRIAL APPLICABILITY

According to the present invention, an inner diameter measuring device comprises an image pickup unit provided at a base end of a frame unit and for picking up an image of a forward end side, a centering unit provided at a forward end of the frame unit, a laser beam diffusing unit provided on the centering unit and at a forward end side of the centering unit via a light transmitting window, a laser beam emitting unit provided on a base end side of the centering unit, and a cone mirror provided on the laser beam diffusing unit and having a conical reflection surface at a forward end, wherein a center line of the cone mirror coincides with an optical axis of the image pickup unit, and the centering unit is adapted to adjust a posture of the image pickup unit so that a laser beam projected from the laser beam emitting unit enters a vertex of the cone mirror. As a result, the optical axis of the laser beam emitting unit can be reliably made coincident with the center line of the cone mirror and the laser beam can be projected in a total circumference in optimal condition. By post-adjustment, the optical axis of the laser beam emitting unit can be reliably made coincident with the center line of the cone mirror, and possible to decrease an accuracy required for parts and to reduce a manufacturing cost.

LEGEND OF REFERENCE NUMERALS

1 Inner diameter measuring device
2 Image pickup unit
3 Laser beam emitting unit
4 Centering unit
5 Laser beam diffusing unit
6 Frame unit
11 Camera
14 Laser emitter
17 Laser beam
17' Laser beam
18 Housing
21 Adjusting mechanism unit
22 X-axis slider
23 Y-axis slider
26 Optical path hole
29 X-axis guide groove
31 X-axis guide
32 Y-axis guide groove
33 Y-axis guide
34 Y-axis guide
36 X-axis adjusting screw
44 Y-axis adjusting screw
51 Cone mirror
52 Total circumferential light transmitting window
55 Light transmitting window
56 Cone mirror holder
57 Fixing flange
61 Optical ring

The invention claimed is:

1. An inner diameter measuring device, comprising an image pickup unit provided at a base end of a frame unit and for picking up an image of a forward end side, a centering unit provided at a forward end of said frame unit, a laser beam diffusing unit provided on said centering unit and at a forward end side of said centering unit via a light transmitting window, a laser beam emitting unit positioned between said centering unit and said image pickup unit and provided on a base end side of said centering unit, and a cone mirror provided on said laser beam diffusing unit and having a conical reflection surface at a forward end, wherein said centering unit has an adjusting mechanism unit comprising an X-axis slider slidable in a direction perpendicularly crossing said optical axis of said image pickup unit, a Y-axis slider disposed on said X-axis slider perpendicularly crossing said optical axis, and being slidable in a direction perpendicularly crossing a sliding direction of said X-axis slider, and has a mounting surface of a light emitting unit formed on said Y-axis slider, and said laser beam emitting unit is mounted on said mounting surface of said light emitting unit, wherein under a condition where a center line of said cone mirror is coincident with said optical axis of said image pickup unit, an optical axis of said laser beam emitting unit is coincided with said center line of said cone mirror so that a laser beam projected from said laser beam emitting unit enters a vertex of said cone mirror.

2. An inner diameter measuring device according to claim 1, wherein said laser beam emitting unit is mounted on said mounting surface of said light emitting unit by three sets of pulling bolts and pushing bolts each disposed at three points and can adjust tilting of an optical axis of said laser beam emitting unit with respect to the center line of said cone mirror by adjusting said pulling bolts and said pushing bolts.

3. An inner diameter measuring device according to claim 1, wherein said centering unit is removably attached to said frame unit, said centering unit and said frame unit are mounted by engaging style, and by mounting on said frame unit, a center line of said centering unit is adapted to coincide with said optical axis of said image pickup unit.

4. An inner diameter measuring device according to claim 1, wherein said laser beam diffusing unit is mounted by engaging style on said centering unit, and by mounting said laser beam diffusing unit on said centering unit, said center line of said cone mirror is adapted to coincide with said center line of said centering unit.

5. An inner diameter measuring device according to claim 4, wherein said centering unit, said laser beam diffusing unit, and said laser beam emitting unit are integrated with each other, and under the condition that said optical axis of said laser beam emitting unit coincides with said center line of said cone mirror by said centering unit, said centering unit is mounted on said frame unit.

6. An inner diameter measuring device according to claim 1, wherein said centering unit, said laser beam diffusing unit, and said laser beam emitting unit are integrated with each other, and under the condition that said optical axis of said laser beam emitting unit coincides with said center line of said cone mirror by said centering unit, said centering unit is mounted on said frame unit.

\* \* \* \* \*